United States Patent
Sander

(10) Patent No.: US 9,080,611 B2
(45) Date of Patent: Jul. 14, 2015

(54) DRIVE TOOL HAVING AN ANGLED CONNECTOR

(75) Inventor: Jeffrey Duncan Sander, Warwick, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1116 days.

(21) Appl. No.: 12/957,800

(22) Filed: Dec. 1, 2010

(65) Prior Publication Data

US 2012/0143195 A1 Jun. 7, 2012

(51) Int. Cl.
*A61B 17/80* (2006.01)
*F16D 3/207* (2006.01)
*A61B 17/16* (2006.01)
*F16D 3/205* (2006.01)

(52) U.S. Cl.
CPC .............. *F16D 3/207* (2013.01); *A61B 17/162* (2013.01); *F16D 3/2052* (2013.01); *A61B 17/1631* (2013.01)

(58) Field of Classification Search
CPC ............ A61B 17/1615; A61B 17/162; A61B 17/1633; F16D 3/207; B25B 13/481; B25B 15/001; B25B 21/00
USPC .................... 81/177.7, 177.75; 606/79, 80
See application file for complete search history.

(56) References Cited

U.S. PATENT DOCUMENTS

| | | | |
|---|---|---|---|
| 1,499,862 A * | 7/1924 | Eichenberg | 74/7 R |
| 3,448,592 A * | 6/1969 | Von Tersch et al. | 464/50 |
| 5,219,174 A * | 6/1993 | Zurbrugg et al. | 279/82 |
| 5,464,407 A * | 11/1995 | McGuire | 606/86 R |
| 5,515,754 A | 5/1996 | Elkins | |
| 6,102,134 A | 8/2000 | Alsruhe | |
| 6,105,473 A | 8/2000 | Huang | |
| 6,386,074 B1 | 5/2002 | Yang | |
| 6,776,499 B2 * | 8/2004 | Chang | 362/119 |
| 7,278,342 B1 | 10/2007 | Chang | |
| 7,597,031 B2 | 10/2009 | Chiang | |
| 8,215,208 B2 * | 7/2012 | Blackston et al. | 81/177.75 |
| 2006/0260446 A1 | 11/2006 | Chang | |
| 2008/0012245 A1 | 1/2008 | Peters | |

* cited by examiner

*Primary Examiner* — Anu Ramana

(74) *Attorney, Agent, or Firm* — Lerner, David, Littenberg, Krumholz & Mentlik, LLP

(57) ABSTRACT

A tool connecting device has a first member extending along a first axis and has an internal cavity adjacent a first end and a threaded outer surface. A second member extends along a second axis and has a tool at a first end and a joint element at a second end. The joint element is pivotally mounted in the cavity of the first member. The second member has an angled surface intermediate the first and second ends. The angled surface is angled outwardly in a direction from the second to the first end. A sleeve is provided which has a threaded inner bore mounted on the threaded outer surface of the first member and is capable of moving along the first axis. The sleeve has a tapered leading end for contacting the angled surface of the second member. The sleeve is movable on the first member to multiple positions along the first axis each position allowing an angle between the second axis and the first axis to be limited to any angle between 0 degrees and approximately 45 degrees.

24 Claims, 9 Drawing Sheets

DRIVE TOOL HAVING AN ANGLED CONNECTOR

BACKGROUND OF THE INVENTION

The present invention relates to a driving or cutting tool, and more particularly to a driving or cutting tool having a rotatable connection device for rotatably connecting a tool, a fastener, a work piece or a driven member to a driveshaft. The rotatable connection device allows the tool shank, fastener, work piece or the driven member to be selectively secured to the tool driveshaft and to be rotated or driven by the driveshaft and be selectively tiltable or slantable relative to the driveshaft axis while rotating.

Typical driving tools, such as wrenches or screwdrivers, may comprise a connector attaching a drill tool member, a tool bit, a fastener or a work piece in a manner to allow the tool bit, fastener, etc. to be selectively secured to a driveshaft and rotated in concert with the driveshaft and to be tiltable or slantable relative to the driveshaft.

Rotational drivers such as drills or screwdrivers having a pivoting mechanism to allow a drill or other tool to be driven at an angle relative to a driver axis are well known. Some of these tools provide an upper angular limit for the angle of the axis of the driven tool to the axis of the driveshaft. Many drive tools provide a method of locking the tool at this maximum angle and also locking the tool when the axis of the drive tool is parallel or collinear with the axis of the driveshaft.

BRIEF SUMMARY OF THE INVENTION

It has been found, especially in surgical applications, that providing the ability for adjusting the maximum angle of the driveshaft axis to the driven tool axis, for example, 45° to 0° (coaxial), continuously or at relatively small discrete increments provides various advantages. The more the angle is between shaft and drill bit axis, the less stable the bit is on the surface to be drilled. Also, increasing this angle increases the difficulty in applying a force in-line with the bit axis of rotation thus making the drilling operation more difficult (especially in case with hard sclerotic bone). Ideally, the shaft should be in-line with the axis of the cutting attachment, but anatomical limitations and exposure difficulties often prevent this. Allowing incremental angle adjustments allows for maximizing the downward (axial) force component under these circumstances. For example, during a drilling operation onto bone, the initial drilling can take place at an angle between the driveshaft and the drill bit of, for example 45° and then gradually and continuously change to 0°, when the axis of the drive shaft and driver tool are collinear, so that the full torque of the rotary power tool driving the driveshaft can be transferred to the drill bit and force can be applied in-line with the axis of rotation of the bit and in direction of cutting (i.e. downward).

This ability may be provided by a tool connection or coupling device which has a first member extending along a first axis, which first member has an internal cavity adjacent a first end of the first member and has a threaded outer surface. The tool has a second member extending along a second axis having a driver member such as a drill or screwdriver at a first end and a joint element at a second end. The joint element of the second member is pivotally mounted in the cavity of the first member. The joint may be a ball and socket joint and/or universal joint.

The second member has an angled surface intermediate the first and second ends, the angled surface angled outwardly in a direction from the second to the first ends i.e. from adjacent the joint to a wider portion adjacent the drill or driver. A sleeve having a threaded inner bore is mounted on the threaded outer surface of the first member and is capable of moving along the first axis toward and away from the angled surface of the second member. The sleeve has a leading tapered end for contacting the angled surface of the second member. The sleeve on the first member is movable to multiple positions along the first axis via rotation on the engaged threads. Each position allows for an angle between the second axis and the first axis to be limited to any angle between, for example, 0 and 45°. Obviously, larger or smaller angles can be provided by varying the angle of the tapered portion on the sleeve or the angled portion on the second member in the area where they contact.

In one embodiment of the present invention, the cavity of the first member has a pivot pin extending therethrough in a direction perpendicular to the first axis. The second end of the second member has a bore therethrough for receiving the pivot pin. The second end of the second member may be generally spherical such as a ball joint or it might be a u-joint or use gears (bevel, etc.). When a ball joint is used the bore extends through an equatorial region of the spherical second end portion in a direction generally perpendicular to the second axis. The bore may intersect a pair of grooves in the outer circumference of the spherical portion which grooves extend generally parallel to the second axis. The grooves allow rotation of the second end of the second member in a direction parallel to the axis of the pivot pin.

The rotation element of the second member includes a part-spherical outer surface and the first member cavity includes a part-spherical inner surface. A part-spherical outer surface of the rotation element rotates on the part spherical inner surface of the first member as the second element is rotated about the pivot pin either along the pivot pin axis or at a angle to the pivot pin axis when the second member is rotated so that part of the grooves in the rotation element contact the pin.

The angled surface of the second member, which tapers outwardly from the second end to the first end thereof, may taper at an angle of approximately 45°. The angled surface can be in the form of a frustro-conical body of rotation utilizing the 45° angle. Other angles could also be used. The first end of the second member can include a cutting tool such as a drill, an awl, a burr, and a reamer as well driving tools such as a screw or nut driver. These tools may be coupled to the second member in any known manner.

The first member is driven by a power tool such as an electric or pneumatic power tool or by hand. The driveshaft itself may be either solid or may be flexible. The sleeve is threaded onto the threads of the first member and may include a releasable detent system for holding the sleeve in a desired rotational position on the first member. The detent system can provide a desired limit to the movement of the sleeve along the first axis and thus the relative rotation between the first and second member with respect to the first and second axes.

The tool described can be used for drilling a hole in a bone by mounting a drill bit in the first end of the second member and then inserting the drill mounted on the first end of the second member into bone at a desired angle usually between 0 and 45° or up to 75° with the sleeve holding the axis of the second member at the desired angle between 0 and 75° with respect to the axis of the first member. As drilling progresses, the sleeve is rotated in a manner to move the sleeve along the first member toward the second member to gradually reduce the angle between the first member and second member until the first and second axes are collinear. At this point, the angle between the first and second axis is 0°. If a detent system is used on the sleeve the advance can be step wise rather than continuously with the detent allowing, for example, 5° steps.

DETAILED DESCRIPTION

Figure 1A:
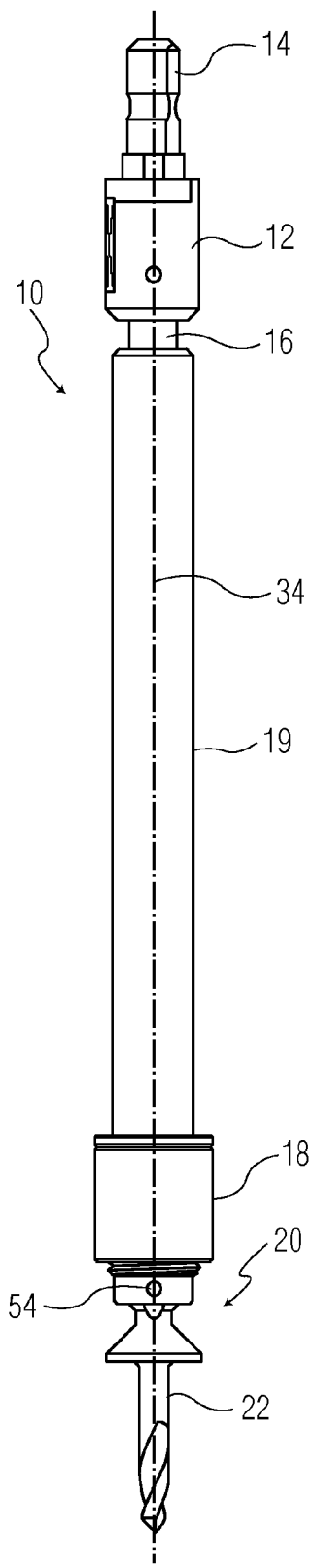
FIG. 1A is a first elevation view of a tool utilizing the connecting device of the present invention with the drill axis aligned with the axis of the drive shaft.
Figure 1B:
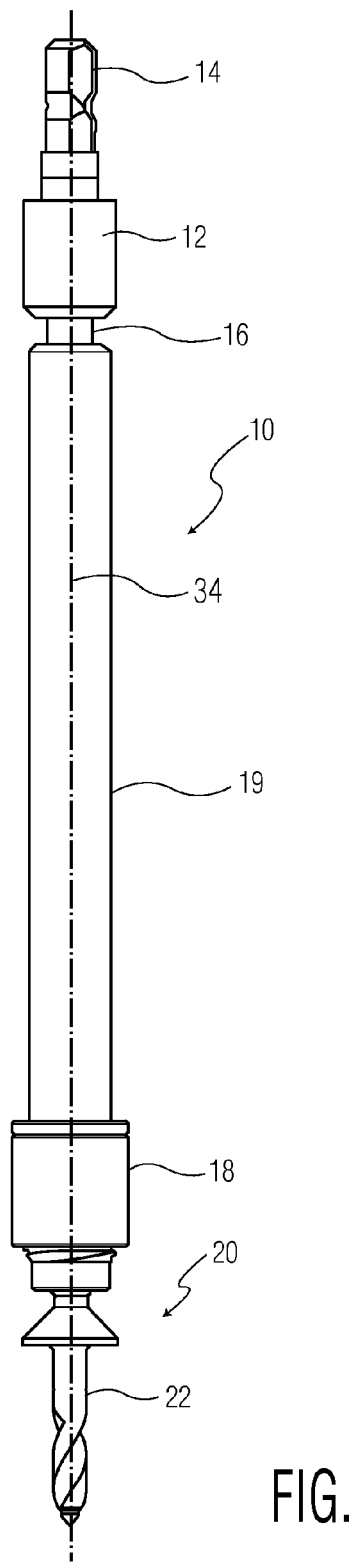
FIG. 1B is a second elevation view of the tool of FIG. 1 rotated 90° about the aligned drill and shaft longitudinal axis.

Referring to FIGS. 1 and 1a there is shown a drive tool generally denoted as 10 having a first driven end 12, including, for example, a drive element 14, adapted to be received in the chuck of an electric or pneumatic power tool or a tool driven by hand. Rotation of the drive element 14 drives a shaft 16, which may be either solid or flexible. The drive tool 10 includes a second end 18, including a connection element generally denoted as 20, which connects a tool, such as, for example, drill bit 22 to drive shaft 16. A freely rotatable sleeve 19 is mounted on shaft 16 to permit a user to hold the sleeve and guide tool 10. Thus a user can hold sleeve 19 stationary while shaft 16 rotates within a hollow bore of sleeve 19.

Figure 2:
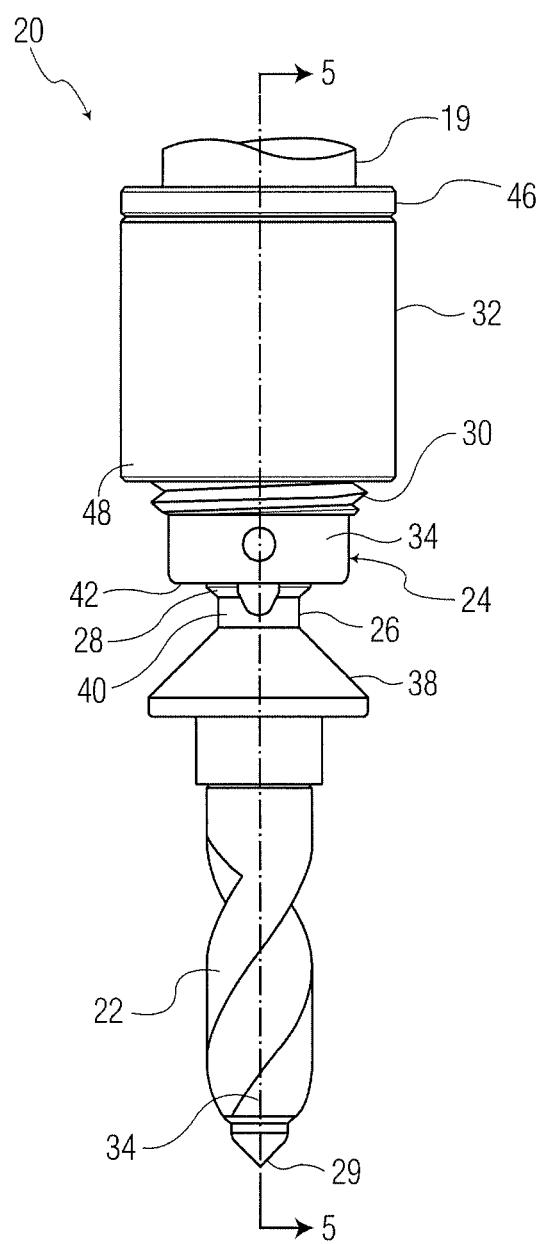
FIG. 2 is an enlarged view of the driving end of the tool of FIGS. 1A and 1B with the connecting device of the present invention showing a sleeve thereon in a first position.
Figure 3:
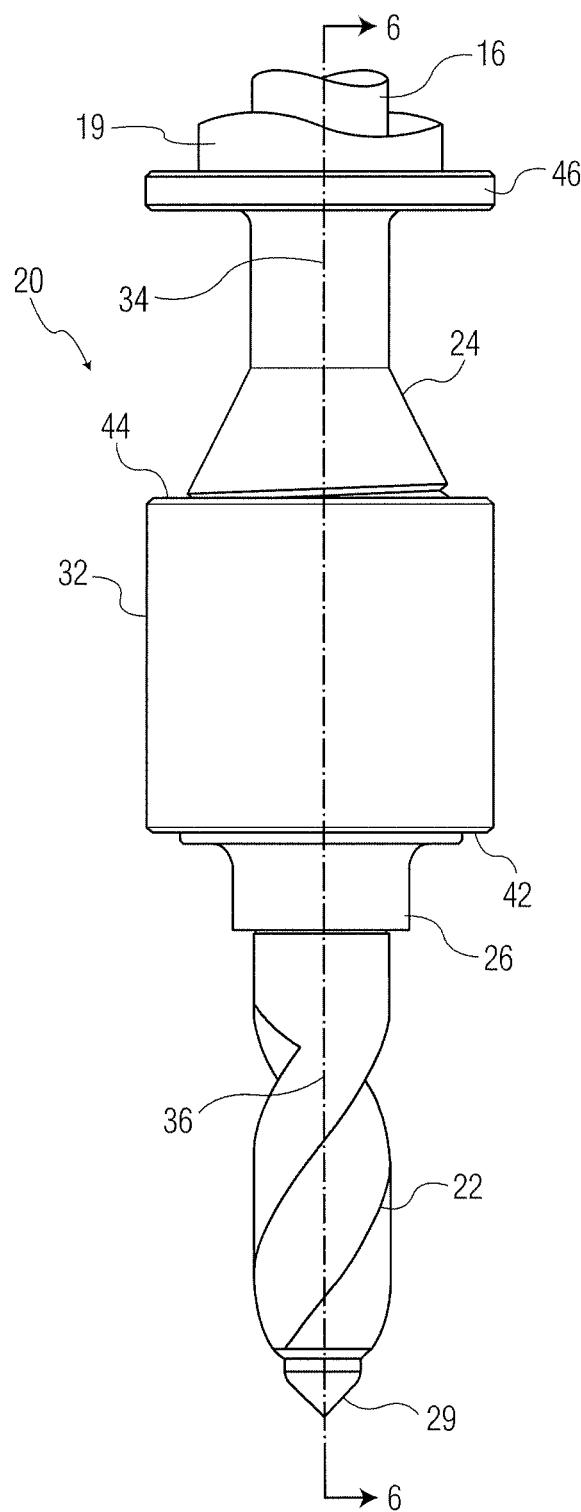
FIG. 3 is a view of FIG. 2 with the sleeve of the connecting device in a second position.
Figure 4:
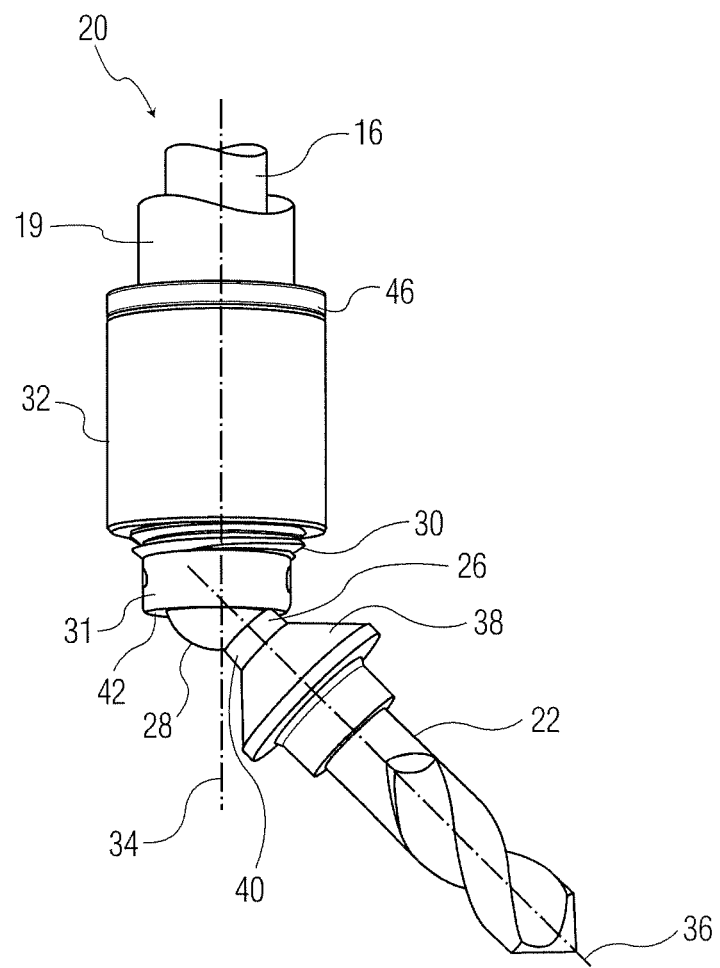
FIG. 4 is a view of the connection device of FIG. 2 with the sleeve in the first position and a drill rotated at an angle with respect to the drive axis of the tool.

Referring to FIGS. 2-4, there is shown an enlarged view of connecting element 20, which includes a first member 24 which is fixed to shaft 16 for rotation therewith, a second member 26, which includes a first end having drill bit 22 mounted thereon and a second end including a part spherical joint portion 28. First member 24 includes a threaded portion 30 on an outer surface 31. A sleeve 32 is threadably mounted on threads 30. Thus, rotation of sleeve 32 in one direction advances the sleeve along a first longitudinal axis 34 toward second member 26. Rotation of sleeve 32 in the other direction moves the sleeve towards shaft 16. As seen in FIG. 4, second member 26 can be pivoted with respect to first member 24 such that a second longitudinal axis 36 thereof forms an angle with axis 34 of first member 24. Axis 34 is also the rotational axis of the driveshaft 16.

As sleeve 32 is rotated in a first direction it engages an outwardly angled surface 38 of second member 26. Angled surface 38 may be a frustro-conical section extending at approximately a 45° angle outwardly from part spherical portion 28 toward a tip 29 of drill bit 22 of second member 26. As sleeve 32 is rotated in the first direction and advances it will contact surface 38. The advance of sleeve 32 on threads 30 may be continuous or if a detent system is used may be in increments of, for example, 5°. As sleeve 32 advances the angle between axes 34 and axes 36 is reduced until, as shown in FIG. 3, the axes are co-linear.

The maximum angle between axes 36 and axes 34 is limited by the contact of a cylindrical portion 40 of second member 26 and a rim 42 which surrounds a cavity 52 (best seen in FIG. 6) within first member 24. Typically, the maximum angle between axes 34 and 36 is between about 30 and 45°. Of course, this maximum angle can only occur when sleeve 32 is rotated in a second direction opposite from the first direction to be spaced from angled surface 38 so that portion 40 of second member 26 contacts rim 42. This second direction rotation of sleeve 32 is limited by the contact of an upper surface 44 of sleeve 32 against a stop plate 46, which is integrally formed with first member 24. Upon full rotation in the first direction of sleeve 32 an end 48 thereof contacts angled surface 38 as will be described in more detail below.

Figure 5:
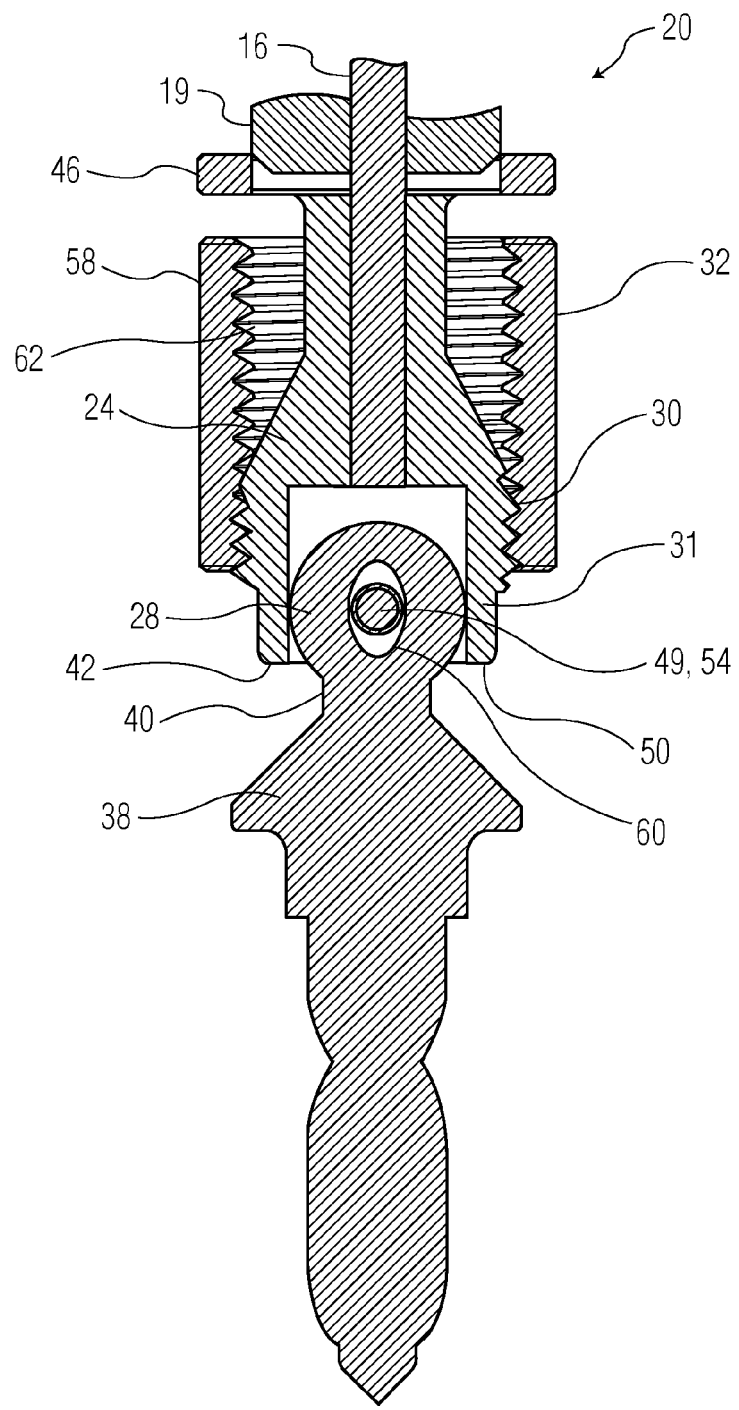
FIG. 5 is a cross-sectional view of the drive end connection device of FIG. 2 along line 5-5.
Figure 6:
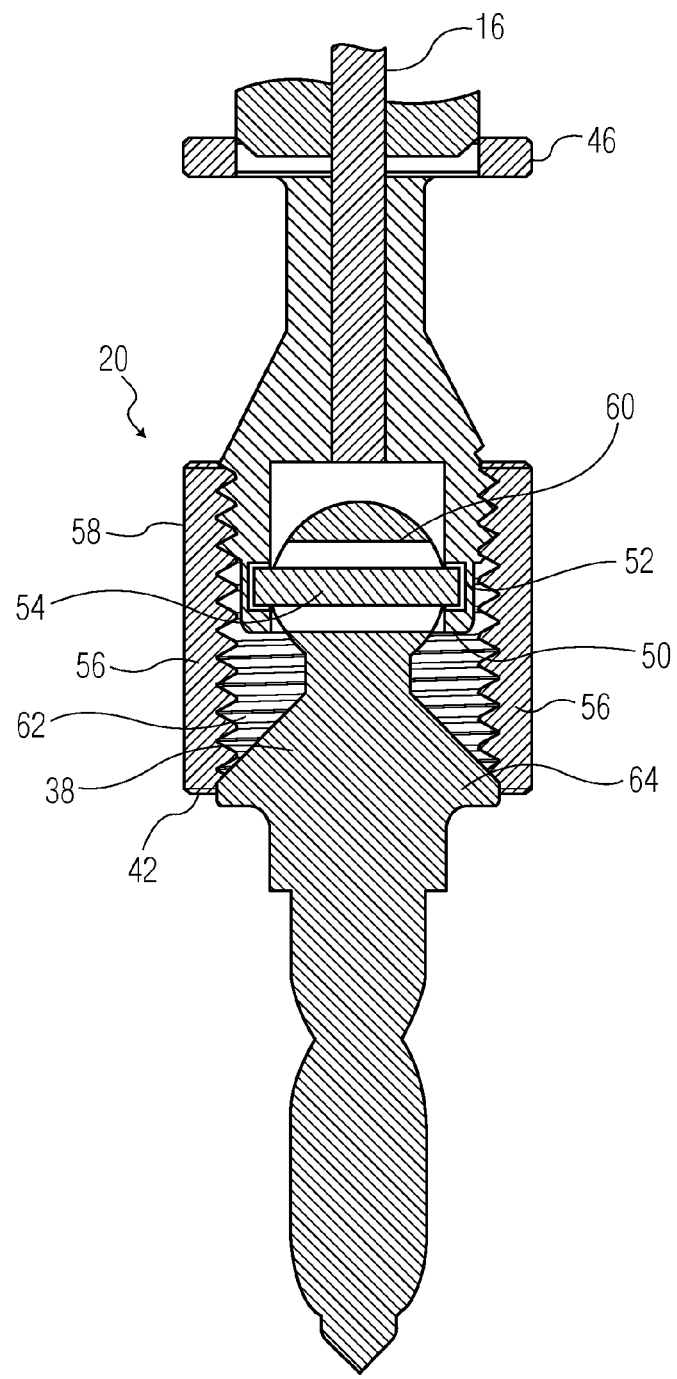
FIG. 6 is a cross-sectional view of the connection device of FIG. 3 along lines 6-6.

Referring to FIGS. 5 and 6, there is shown cross-sectional views of the connecting element 20. The cross-sectional views show the threading 50 on an inner surface of sleeve 32, which threading 50 engages threading 30 on the outer surface 31 of first member 24. In addition, in FIG. 6, there is shown cavity 52 internal to first member 24. Cavity 52 is preferably part spherical and forms a socket for receiving part spherical joint portion on second member 26. Cavity 52 and the outer surface 31, which includes threaded portion 30, define a wall through which a pair of holes 49 and 51 extend. Holes 49 and 51 receive a pivot pin 54, which extends through cavity 52.

Referring to FIGS. 5-9, there is shown second member 26 with part-spherical joint portion 28 having a bore 60 therethrough for receiving pivot pin 54. During manufacture of connecting element 20, sleeve 32 is threadably attached to first member 24 and moved into contact with stop member 46. Then part spherical head 28 is inserted into part spherical cavity 52 with hole 60 aligned with the holes or bores 49 and 51 in first member 24. Hole 60, as shown in F*igure* 5, is non-circular i.e., oval. Pin 54 is then inserted through the aligned bores 49, 51, and 60 and spot welded or otherwise permanently fixed within bores 49 and 51 of first member 24. This allows second member 26 to pivot around pin 54 and allows pin 54 to drive second member 26 as drive shaft 16 is driven.

As can be seen in FIGS. 5 and 6, sleeve element 32 includes an annular wall 56 which extends between an outer surface 58 thereof and inner threaded portion 50, which walls define an opening 62, which includes an inner tapered contact surface 64 designed to contact angled surface 38. Surfaces 38 and 64 may have the same angle. As shown in FIG. 3, when sleeve 32 is at its maximum location achieved by the rotation thereof in the first direction, axes 34 and 36 are coaxial, that is, at a 0° angle, and surface 64 is adjacent a lower end of frustro-conical surface 38. As the sleeve 32 is rotated in the second direction, a gap occurs between angled surface 38 and tapered surface 64 of sleeve 32 so that some angular rotation of axis 36 of second member 26 is possible with respect to axis 34 of first member 24. This angle, or gap size, can be very finely adjustable depending on the pitch of threads 30 and 50, thus allowing a continuously variable limit on the angulation between axes 34 and 36 from 0° to 45°. As stated above, the maximum angle at any given location of sleeve 32 is determined by the contact of rim 42 of first member 24 and cylindrical surface 40 of member 26. Locking at 0° occurs when sleeve 32 is moved a sufficient distance toward and tapered surface 64 of angled surface 38.

Figure 7:
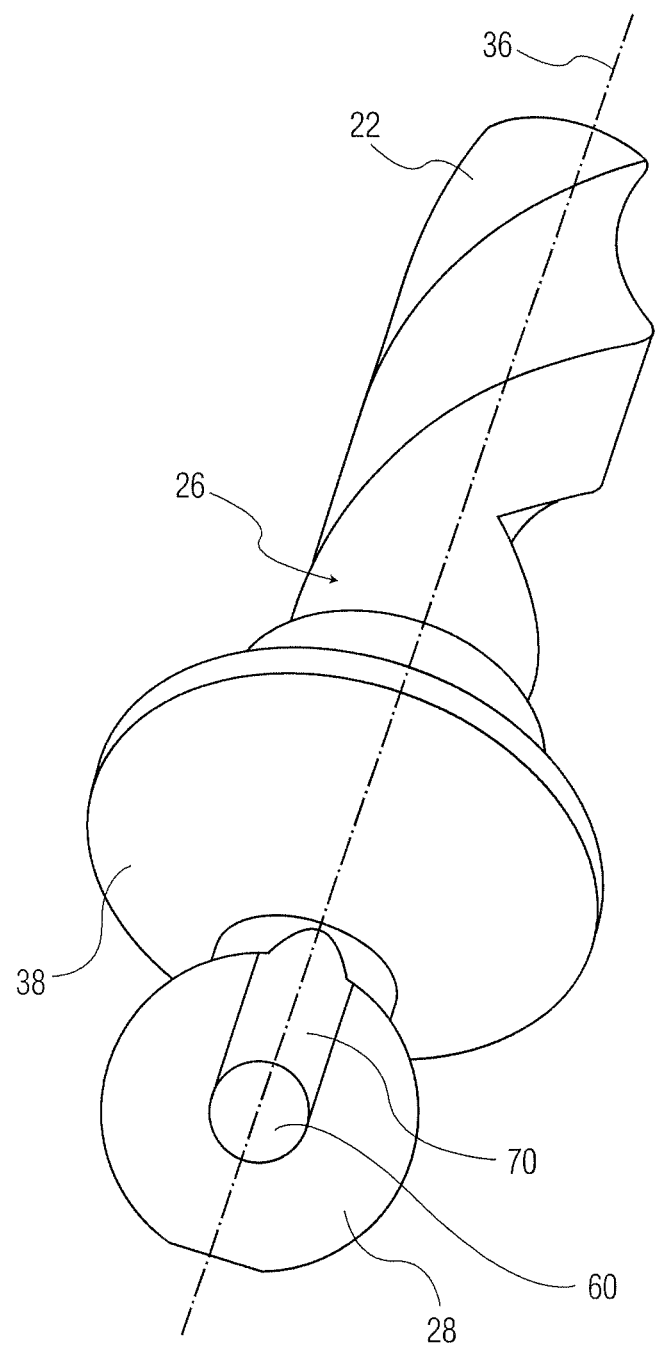
FIG. 7 is an isometric view of the second element of the connection element.
Figure 8:
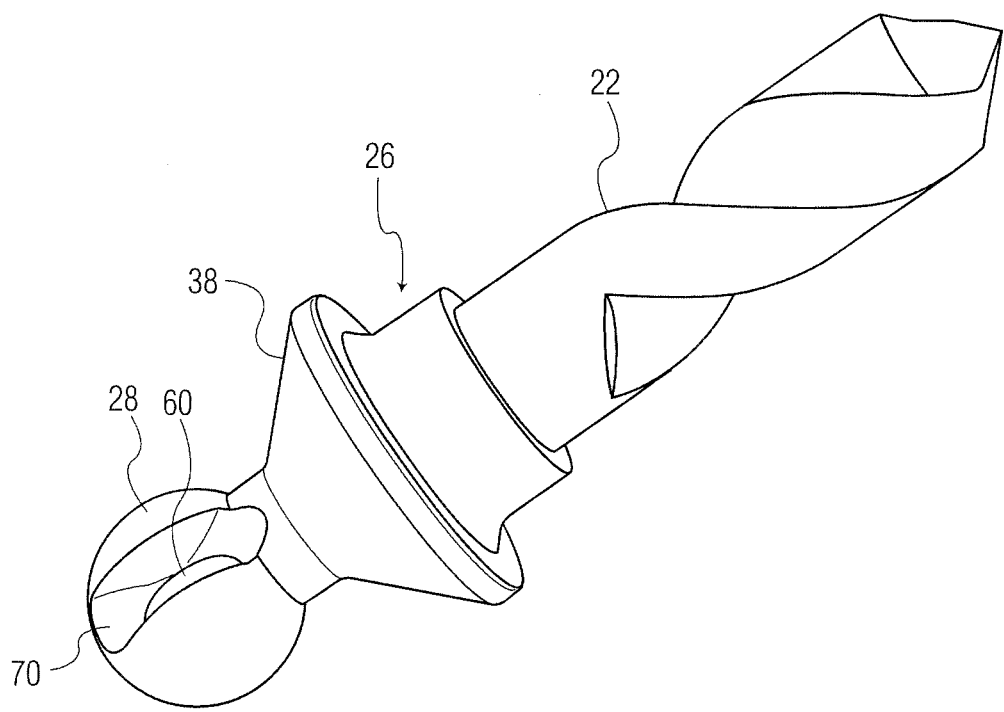
FIG. 8 is a second isometric view of the second member of the connection element.
Figure 9:
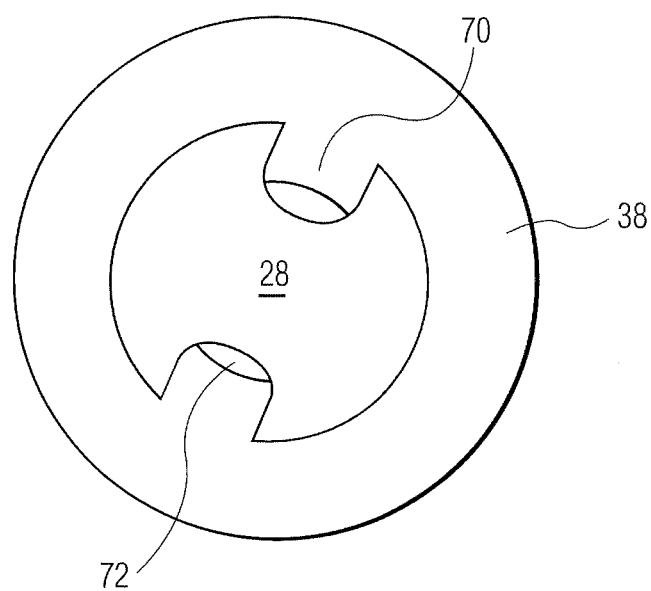
FIG. 9 is a top view of the second member of the connection element shown in FIGS. 7 and 8.

As best seen in FIGS. 7-9, part spherical joint portion 28 of second member 26 includes a pair of grooves 70 and 72, which intersect hole 60 and extend parallel to axis 36 of second member 26. Grooves 70 and 72 allow limited rotation of second member 26 in a direction parallel to the axis of pivot pin 54. The rotation allowed in this direction is sufficient to obtain the maximum angle, for example, 45° or even up to 90° which may be attainable with use of bevel gears.

While the connecting element 20 can be used with the angle between axes 34 and 36 set by the sleeve 32 location to any desired angle such as, for example, between 0 and 45°, it can also be utilized to vary the angle during use such as during the drilling operation. In this case, such as during drilling a bore in bone, the operator or surgeon would initially set the maximum angle by locating sleeve 32 in a desired position along axis 34 toward drive shaft 16 and then, after drilling is initiated, gradually rotate sleeve 32 clockwise thus advancing the sleeve and rim 48 and its inner tapered surface 64 against angled surface 38 of second element 26 to gradually reduce the maximum angle until, if desired, the angle is 0°. This is advantageous because, as discussed above, as the angle decreases the component of applied force not acting in-line with the drive axis decreases so that more force can be applied to drilling the bore.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tool connecting device comprising:
a drive shaft;
a first member fixed to the drive shaft extending along a first axis, the first member having an outer circumferential surface and an inner circumferential surface defining a wall therebetween, the inner circumferential surface surrounding a cavity having an open end, a connection element mounted in the wall and extending into the cavity;
a second member extending along a second axis having a tool at a first end and a joint element at a second end, the joint element mounted in the cavity of the first member and pivotally mounted on the connection element of the first member, the second member having an angled surface intermediate the first and second ends, the angled surface angled outwardly in a direction from the second end to the first end of the second member, the second member coupled to the first member for rotation therewith;
and a sleeve having an inner bore adjustably mounted on the outer surface of the first member capable of moving along the first axis, the sleeve having a leading end for contacting the angled surface of the second member, the sleeve movable on the first member to multiple positions along the first axis each position allowing an angle between the second axis and the first axis to be an angle between 0 degrees and 75 degrees; and
wherein the first member connection element includes a pivot pin mounted on the first member and extending through the cavity and the second member joint element has a bore for receiving the pivot pin, the bore defined by first and second ends, each of the first and second ends of the bore intersected by a groove extending parallel to the second axis.

2. The tool connecting device as set forth in claim 1, wherein the first member cavity has a part-spherical concave inner surface and the joint element of the second member has a part-spherical convex outer surface for engaging the part-spherical inner surface of the first member cavity.

3. The tool connecting device as set forth in claim 1, wherein the second member joint element includes a part spherical outer surface and the first member cavity includes a part spherical inner surface.

4. The tool connecting device as set forth in claim 3 wherein the part-spherical outer surface of the second member joint element includes the bore for receiving the pivot pin.

5. The tool connecting device as set forth in claim 4, wherein the part spherical outer surface of the second member has the pair of grooves extending parallel to the second axis.

6. The tool connecting device as set forth in claim 5, wherein a first end of the groove intersects the bore in the part spherical outer surface of the joint element and a second end of the groove is open to the part-spherical outer surface and extends along an axis spaced from the second axis.

7. The tool connecting device as set forth in claim 1, wherein the angled surface of the second member tapers outwardly at an angle of 45°.

8. The tool connecting device as set forth in claim 1, wherein the tool at the first end of the second member is selected from the group consisting of a drill, a screwdriver, an awl, a burr, and a reamer.

9. The tool connecting element as set forth in claim 1, wherein the angled surface of the second member is a frustro-conical surface extending around the second axis.

10. The tool connecting element as set forth in claim 1, wherein the first member has a drive shaft coupled to a second end.

11. The tool connecting element as set forth in claim 1 further comprising a means for holding the sleeve in a desired rotational position on the first member.

12. The tool as set forth in claim 1 wherein the sleeve is threadably mounted on the outer surface of the first member.

13. The tool as set forth in claim 1 wherein the bore is oval in cross-section.

14. A tool connecting device comprising:
a drive shaft;
a first member fixed to the drive shaft extending along a first axis, the first member having an outer circumferential surface and an inner circumferential surface defining a wall therebetween, the inner circumferential surface surrounding a cavity having an open end, a connection element mounted in the wall and extending into the cavity;
a second member extending along a second axis having a tool at a first end and a joint element at a second end, the joint element mounted in the cavity of the first member and pivotally mounted on the connection element of the first member, the second member having an angled surface intermediate the first and second ends, the angled surface angled outwardly in a direction from the second end to the first end of the second member, the second member coupled to the first member for rotation therewith;
and a sleeve having an inner bore adjustably mounted on the outer surface of the first member capable of moving along the first axis, the sleeve having a leading end for contacting the angled surface of the second member, the sleeve movable on the first member to multiple positions along the first axis each position allowing an angle between the second axis and the first axis to be an angle between 0 degrees and 75 degrees; and
wherein the first member connection element includes a pivot pin mounted on the first member and extending through the cavity and the second member joint element has a bore for receiving the pivot pin, the bore defined by a first and a second end, each of the first and second ends of the bore in the second member joint elements intersected by a respective first and second groove in the joint element, which first and second grooves are open to an outer surface of the joint element.

15. The tool connecting device as set forth in claim 14, wherein the first member cavity has a part-spherical concave inner surface and the joint element of the second member has a part-spherical convex outer surface for engaging the part-spherical inner surface of the first member.

16. The tool connecting device as set forth in claim 14, wherein the second member joint element includes a part spherical outer surface and the first member cavity includes a part spherical inner surface.

17. The tool connecting device as set forth in claim 16 wherein the part-spherical outer surface of the second member joint element includes the bore for receiving the pivot pin.

18. The tool connecting device as set forth in claim 17, wherein the part spherical outer surface of the second member has the pair of grooves extending parallel to the second axis.

19. The tool connecting device as set forth in claim 18, wherein a first end of the groove intersects the bore in the part spherical outer surface of the joint element and a second end of the groove is open to the part-spherical outer surface and extends along an axis spaced from the second axis.

20. The tool connecting device as set forth in claim 14, wherein the angled surface of the second member tapers outwardly at an angle of 45°.

21. The tool connecting device as set forth in claim 14, wherein the tool at the first end of the second member is selected from the group consisting of a drill, a screwdriver, an awl, a burr, and a reamer.

22. The tool connecting element as set forth in claim 14, wherein the angled surface of the second member is a frustro-conical surface extending around the second axis.

23. The tool connecting element as set forth in claim 14, wherein the first member has a drive shaft coupled to a second end.

24. The tool connecting element as set forth in claim 14 further comprising a means for holding the sleeve in a desired rotational position on the first member.

\* \* \* \* \*